(12) United States Patent
Leadley (10) Patent No.: US 12,426,640 B2
(45) Date of Patent: Sep. 30, 2025

(54) SYSTEM AND METHOD OF CONSUMPTION CONTROL FOR AN ELECTRONIC VAPOR PROVISION SYSTEM

(71) Applicant: Nicoventures Trading Limited, London (GB)

(72) Inventor: David Leadley, London (GB)

(73) Assignee: NICOVENTURES TRADING LIMITED, London (GB)

( * ) Notice: Subject to any disclaimer, the term of this patent is extended or adjusted under 35 U.S.C. 154(b) by 729 days.

(21) Appl. No.: 17/294,319

(22) PCT Filed: Oct. 4, 2019

(86) PCT No.: PCT/GB2019/052806
§ 371 (c)(1),
(2) Date: May 14, 2021

(87) PCT Pub. No.: WO2020/099824
PCT Pub. Date: May 22, 2020

(65) Prior Publication Data
US 2022/0007736 A1     Jan. 13, 2022

(30) Foreign Application Priority Data
Nov. 16, 2018   (GB) ..................... 1818743

(51) Int. Cl.
*A24F 40/53*   (2020.01)
*A24F 40/51*   (2020.01)
(Continued)

(52) U.S. Cl.
CPC .............. *A24F 40/53* (2020.01); *A24F 40/51* (2020.01); *A24F 40/60* (2020.01); *A24F 40/65* (2020.01)

(58) Field of Classification Search
None
See application file for complete search history.

(56) References Cited

U.S. PATENT DOCUMENTS

| 6,886,557 B2 | 5/2005 | Childers et al. |
| 7,250,035 B1 | 7/2007 | Ott et al. |

(Continued)

FOREIGN PATENT DOCUMENTS

| CN | 1633247 A | 6/2005 |
| CN | 106535673 A | 3/2017 |

(Continued)

OTHER PUBLICATIONS

Dialog Semiconductor, "DA14580—Low Power Bluetooth Smart SoC," Retrieved from http://www.dialog-semiconductor.com/products/bluetooth-smart/smarttbond-da-14580, ® 2014, Jan. 29, 2015, Version. 3.1, 158 pages.

(Continued)

*Primary Examiner* — Michael H. Wilson
*Assistant Examiner* — Michael T Fulton
(74) *Attorney, Agent, or Firm* — Burr & Forman (57) ABSTRACT

An active ingredient adjustment system for an electronic vapor provision system (EVPS), comprises a memory configured to store data indicating a target amount of active ingredient to be delivered by the EVPS within a predetermined period having a predetermined start point; a payload usage sensor configured to detect the amount of payload being used; a usage timing processor configured to calculate the rate of active ingredient being delivered to the user based upon the amount of payload being used; and an adjustment processor adapted to alter the operation of the EVPS to reduce the rate of active ingredient being delivered to the user in response to the usage timing processor calculating a rate of active ingredient being delivered that will result in exceeding the target within the predetermined period.

10 Claims, 7 Drawing Sheets

(51) Int. Cl.
*A24F 40/60* (2020.01)
*A24F 40/65* (2020.01)

(56) References Cited

U.S. PATENT DOCUMENTS

| | | |
|---|---|---|
| 2011/0265806 A1 | 11/2011 | Alarcon et al. |
| 2013/0284192 A1 | 10/2013 | Peleg et al. |
| 2013/0340775 A1 | 12/2013 | Juster et al. |
| 2014/0224245 A1 | 8/2014 | Alelov |
| 2015/0272220 A1 | 10/2015 | Spinka et al. |
| 2016/0089508 A1 | 3/2016 | Smith et al. |
| 2016/0106936 A1 | 4/2016 | Kimmel |
| 2016/0157524 A1 | 6/2016 | Bowen et al. |
| 2016/0331027 A1 | 11/2016 | Cameron |
| 2016/0337362 A1 | 11/2016 | Cameron |
| 2017/0181474 A1 | 6/2017 | Cameron |
| 2017/0251727 A1 | 9/2017 | Nielsen |
| 2018/0043114 A1 | 2/2018 | Bowen et al. |

FOREIGN PATENT DOCUMENTS

| | | |
|---|---|---|
| CN | 102333566 A | 9/2017 |
| CN | 108495665 A | 9/2018 |
| EP | 1415677 A1 | 6/2004 |
| GB | 2524817 A | 10/2015 |
| RU | 2595593 C2 | 8/2016 |
| WO | WO2016090303 A1 | 6/2016 |
| WO | WO2016199062 A1 | 12/2016 |
| WO | 2017184777 A1 | 6/2017 |
| WO | WO2020128431 | 6/2020 |

OTHER PUBLICATIONS

IEEE, 802.15.1 (Jun. 14, 2002) IEEE Standard for Telecommunications and Information Exchange Between Systems—LAN/MAN—Specific Requirements Part 15: Wireless Medium Access Control (MAC) and Physical Layer (PHY) Specifications for Wireless Personal Area Networks (WPANs), 2 pages.
IEEE, IEEE Publishes the 802.11v Amendment Titled Wireless Network Management to Extend the Base IEEE 802.11 .TM. Wireless LAN Standards (May 13, 2011), 1 page.
IEEE Standards Association, "P802.11ah—IEEE Draft Standard for Information Technology—Telecommunications and Information Exchange Between Systems—Local and Metropolitan Area networks—Specific Requirements—Part 11: Wireless LAN Medium Access Control (MAC) and Physical Layer," 2016, 1 page.
Office Action For Russian Application No. 2021113559, mailed on Nov. 9, 2021, 8 pages.
Search Report for Great Britain Patent Application No. GB1818743.5, dated May 10, 2019, 6 pages.
International Search Report and Written Opinion for PCT/GB2019/052806, dated Jan. 2, 2020, 20 pages.
Notice of the Third Office Action and Search Report from the corresponding CN Application No. 2019800753492, mailed Mar. 11, 2025, all pages cited in its entirely.

SYSTEM AND METHOD OF CONSUMPTION CONTROL FOR AN ELECTRONIC VAPOR PROVISION SYSTEM

PRIORITY CLAIM

The present application is a National Phase entry of PCT Application No. PCT/GB2019/052806, filed Oct. 4, 2019, which claims priority from Great Britain Application No. 1818743.5, filed Nov. 16, 2018, each of which is hereby fully incorporated herein by reference.

TECHNICAL FIELD

The present invention relates to a system and method of consumption control.

BACKGROUND

Users of traditional cigarettes have a straightforward mechanism by which to monitor their consumption, e.g. the number of cigarettes consumed per day. However, it can be less straightforward for a user to monitor their consumption when using an e-cigarette, as the payload used as a vapor source (for example an E liquid reservoir) may be physically hidden from the user within an e-cigarette/vapor provision system. Even if visible, it may not be easy to tell how much liquid has been consumed within a given period, particularly since a 10 ml reservoir may typically be expected to last up to a week.

Furthermore, different e-liquids can have different concentrations of active ingredient (for example nicotine), and so a like-for-like visual gauge of payload consumption may not reliably indicate the amount of active ingredient consumed within a given period.

The present invention seeks to address, alleviate or mitigate this problem.

SUMMARY

In a first aspect, an active ingredient adjustment system for an electronic vapor provision system (EVPS), including a memory adapted to store data indicating a target amount of active ingredient to be delivered by the EVPS within a predetermined period having a predetermined start point, a payload usage sensor configured to detect the amount of payload being used, a usage timing processor configured to calculate the rate of active ingredient being delivered to the user based upon the amount of payload being used; and an adjustment processor configured to alter the operation of the EVPS to reduce the rate of active ingredient being delivered to the user in response to the usage timing processor calculating a rate of active ingredient being delivered that will result in exceeding the target within the predetermined period.

In another aspect, an EVPS, including an active ingredient adjustment system including a payload usage sensor operable to detect the amount of payload being used; and the active ingredient adjustment system being configured to alter operation of the EVPS in response to control signals from an adjustment processor configured to alter the operation of the EVPS to reduce the rate of active ingredient being delivered to a user of the EVPS in response to a usage timing processor calculating a rate of active ingredient being delivered that will result in exceeding a target amount of active ingredient to be delivered by the VPS within a predetermined period having a predetermined start point.

In another aspect, a mobile communication device including a wireless receiver configured to receive data from an EVPS indicative of an amount of payload being used by a user, a wireless transmitter configured to transmit control data to the EVPS, and an active ingredient adjustment system having a usage timing processor configured to calculate the rate of active ingredient being delivered to the user based upon the amount of payload being used, and an adjustment processor configured to generate control data for altering the operation of the EVPS to reduce the rate of active ingredient being delivered to the user in response to the usage timing processor calculating a rate of active ingredient being delivered that will result in exceeding a target within a predetermined period having a predetermined start point.

In another aspect, a method of active ingredient adjustment for an EVPS, including storing data indicating a target amount of active ingredient to be delivered by the EVPS within a predetermined period having a predetermined start point, detecting the amount of payload being used, calculating the rate of active ingredient being delivered to the user based upon the amount of payload being used, and altering the operation of the EVPS, if the usage timing processor calculates a rate of active ingredient being delivered that will result in exceeding the target within the predetermined period, to reduce the rate of active ingredient being delivered to the user.

Further respective aspects and features of the invention are defined in the appended claims.

BRIEF DESCRIPTION OF THE DRAWINGS

Embodiments of the present invention will now be described by way of example with reference to the accompanying drawings, in which.

DETAILED DESCRIPTION

A system and method of consumption control are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

By way of background explanation, electronic vapor provision systems, such as e-cigarettes and other aerosol delivery systems, generally contain a reservoir of liquid which is to be vaporized, typically nicotine (this is sometimes referred to as an "e-liquid"). When a user inhales on the device, an electrical (e.g. resistive) heater is activated to vaporize a small amount of liquid, in effect producing an aerosol which is therefore inhaled by the user. The liquid may comprise nicotine in a solvent, such as ethanol or water, together with glycerin or propylene glycol to aid aerosol formation, and may also include one or more additional flavors. The skilled person will be aware of many different liquid formulations that may be used in e-cigarettes and other such devices.

The practice of inhaling vaporized liquid in this manner is commonly known as 'vaping'. An e-cigarette may have an interface to support external data communications. This interface may be used, for example, to load control parameters or updated software onto the e-cigarette from an external source. Alternatively or additionally, the interface may be utilized to download data from the e-cigarette to an external system. The downloaded data may, for example, represent usage parameters of the e-cigarette, fault conditions, etc. As the skilled person will be aware, many other forms of data can be exchanged between an e-cigarette and one or more external systems (which may be another e-cigarette).

In some cases, the interface for an e-cigarette to perform communication with an external system is based on a wired connection, such as a USB link using a micro, mini, or ordinary USB connection into the e-cigarette. The interface for an e-cigarette to perform communication with an external system may also be based on a wireless connection. Such a wireless connection has certain advantages over a wired connection. For example, a user does not need any additional cabling to form such a connection. In addition, the user has more flexibility in terms of movement, setting up a connection, and the range of pairing devices.

Throughout the present description the term "e-cigarette" is used; however, this term may be used interchangeably with electronic vapor provision system, aerosol delivery device, and other similar terminology.

Figure 1:
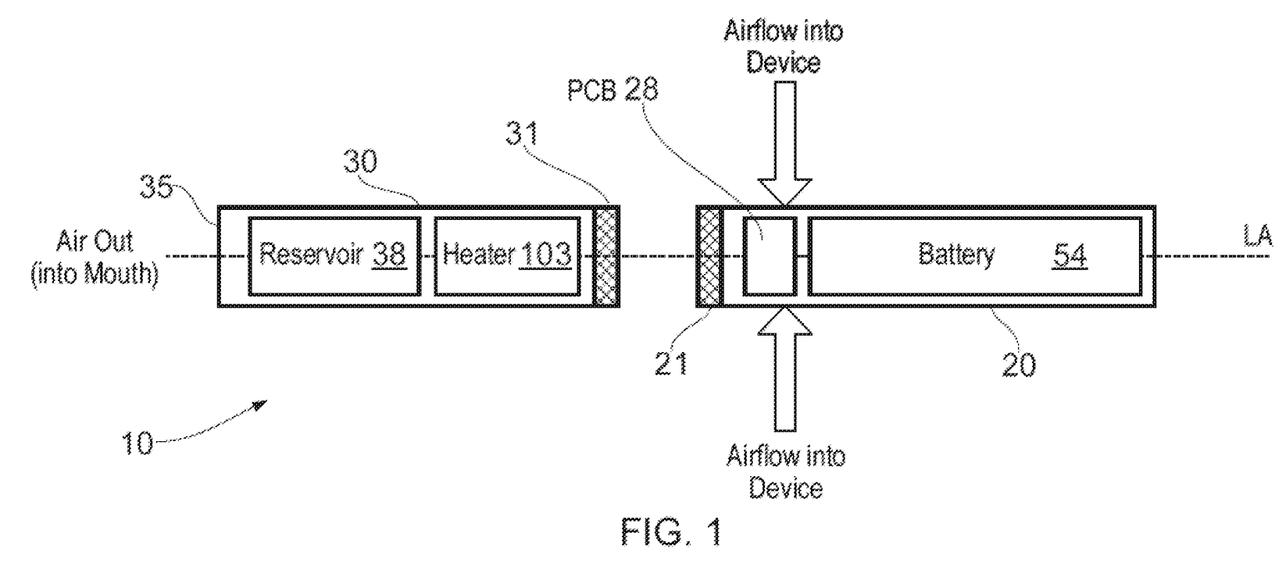
FIG. 1 is a schematic diagram of an e-cigarette in accordance with embodiments of the present invention.

FIG. 1 is a schematic (exploded) diagram of an e-cigarette 10 in accordance with some embodiments of the disclosure (not to scale). The e-cigarette comprises a body or control unit 20 and a cartomizer 30. The cartomizer 30 includes a reservoir 38 of liquid, typically including nicotine, a heater 36, and a mouthpiece 35. The e-cigarette 10 has a longitudinal or cylindrical axis which extends along the center-line of the e-cigarette from the mouthpiece 35 at one end of the cartomizer 30 to the opposing end of the control unit 20 (usually referred to as the tip end). This longitudinal axis is indicated in FIG. 1 by the dashed line denoted LA.

The liquid reservoir 38 in the cartomizer may hold the (e-)liquid directly in liquid form, or may utilize some absorbing structure, such as a foam matrix or cotton material, etc, as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

In other devices, the liquid may be provided in the form of plant material or some other (ostensibly solid) plant derivative material. In this case the liquid can be considered as representing volatiles in the material which vaporize when the material is heated. Note that devices containing this type of material generally do not require a wick to transport the liquid to the heater, but rather provide a suitable arrangement of the heater in relation to the material to provide suitable heating.

It will also be appreciated that forms of payload delivery other than a liquid may be equally considered, such as heating a solid material (such as processed tobacco leaf) or a gel. In such cases, the volatiles that vaporize provide the active ingredient of the vapor/aerosol to be inhaled. It will be understood that references herein to 'liquid', 'e-liquid' and the like equally encompass other modes of payload delivery, and similarly references to 'reservoir' or similar equally encompass other means of storage, such as a container for solid materials.

The control unit 20 includes a re-chargeable cell or battery 54 to provide power to the e-cigarette 10 (referred to hereinafter as a battery) and a printed circuit board (PCB) 28 or other electronics for generally controlling the e-cigarette.

The control unit 20 and the cartomizer 30 are detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit and cartomizer provides for mechanical and electrical connectivity between the two.

When the control unit is detached from the cartomizer, the electrical connection 21A on the control unit that is used to connect to the cartomizer may also serve as a socket for connecting a charging device (not shown). The other end of this charging device can be plugged into a USB socket to re-charge the battery 54 in the control unit of the e-cigarette. In other implementations, the e-cigarette may be provided (for example) with a cable for direct connection between the electrical connection 21A and a USB socket.

The control unit is provided with one or more holes for air inlet adjacent to PCB 28. These holes connect to an air passage through the control unit to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes from the control unit into the vaporizer, where the airflow combines with the nicotine vapor. This combination of airflow and nicotine vapor (in effect, an aerosol) then passes through the cartomizer 30 and out of the mouthpiece 35 to be inhaled by a user. The cartomizer 30 may be detached from the control unit and disposed of when the supply of nicotine liquid is exhausted (and then replaced with another cartomizer).

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette may be provided with a cartomizer 30 as shown in FIG. 1, or else constructed as a one-piece (unitary) device, but the liquid reservoir 38 is in the form of a (user-)replaceable cartridge. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer, and the liquid reservoir is in the form of an annular structure which is radially outside the heater 35.

The skilled person will also be aware of a number of possible variations for the control unit 20. For example, airflow may enter the control unit at the tip end, i.e. the opposite end to connector 21A, in addition to or instead of the airflow adjacent to PCB 28. In this case the airflow would typically be drawn towards the cartomizer along a passage between the battery 54 and the outer wall of the control unit. Similarly, the control unit may comprise a PCB located on or near the tip end, e.g. between the battery and the tip end. Such a PCB may be provided in addition to or instead of PCB 28.

Furthermore, an e-cigarette may support charging at the tip end, or via a socket elsewhere on the device, in addition to or in place of charging at the connection point between the cartomizer and the control unit. (It will be appreciated that some e-cigarettes are provided as essentially integrated units, in which case a user is unable to disconnect the cartomizer from the control unit). Other e-cigarettes may also support wireless (induction) charging, in addition to (or instead of) wired charging.

The above discussion of potential variations to the e-cigarette shown in FIG. 1 is by way of example. The skilled person will aware of further potential variations (and combination of variations) for the e-cigarette 10.

Figure 2:
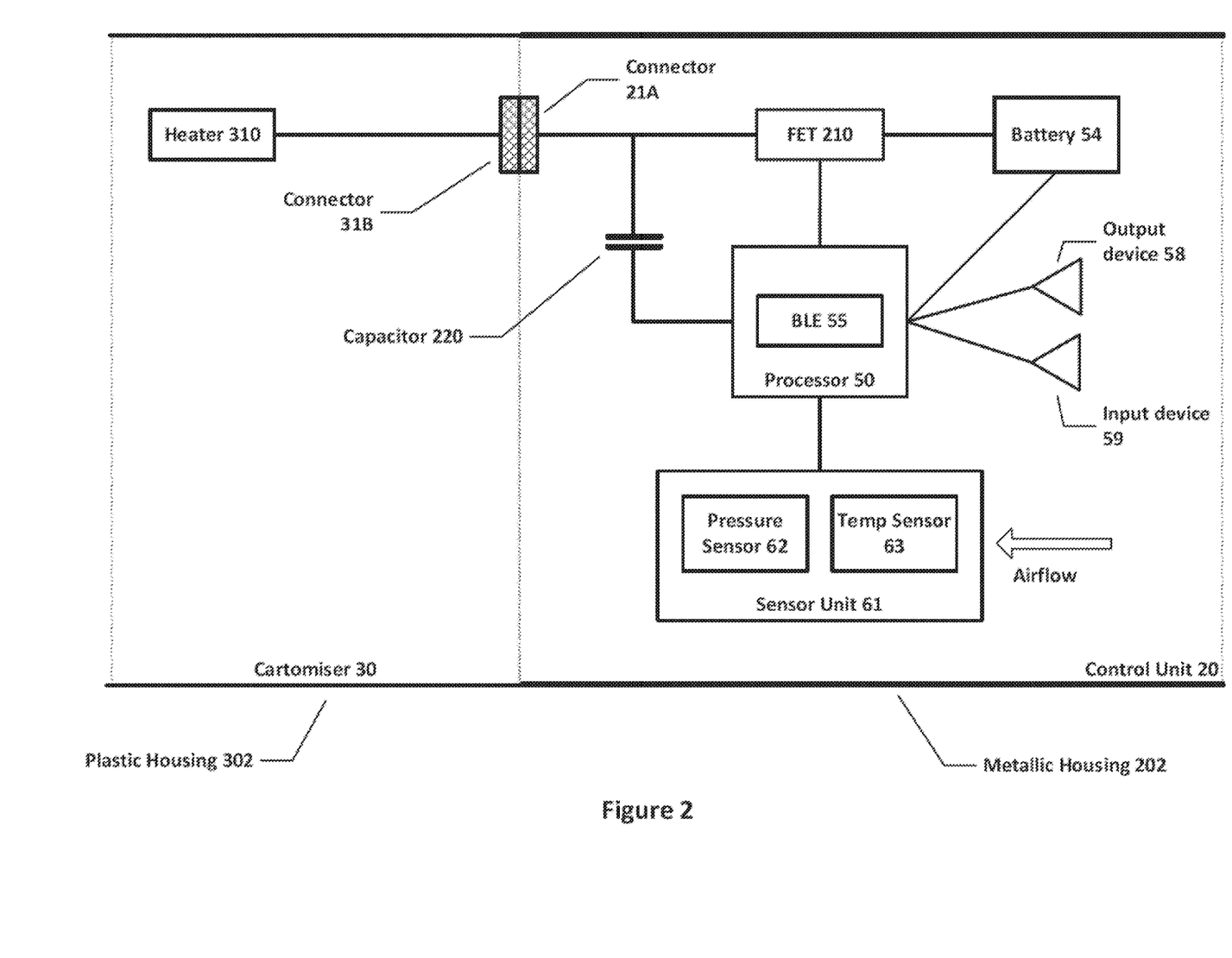
FIG. 2 is a schematic diagram of a control unit of an e-cigarette in accordance with embodiments of the present invention.

FIG. 2 is a schematic diagram of the main functional components of the e-cigarette 10 of FIG. 1 in accordance with some embodiments of the disclosure. N.B. FIG. 2 is primarily concerned with electrical connectivity and functionality—it is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit to operate in conjunction with the circuit board 28, but not physically mounted on the circuit board itself. For example, these components may be located on one or more additional circuit boards, or they may be separately located (such as battery 54).

As shown in FIG. 2, the cartomizer contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit contains a pressure sensor 62 and temperature sensor 63 (also in or adjacent to this air path). The control unit further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio or haptic output. For example, the output device(s) may include a speaker 58, a vibrator, or one or more lights. The lights are typically provided in the form of one or more light emitting diodes (LEDs), which may be the same or different colors (or multi-colored). In the case of multi-colored LEDs, different colors are obtained by switching different colored, e.g. red, green or blue, LEDs on, optionally at different relative brightnesses to give corresponding relative variations in color. Where red, green and blue LEDs are provided together, a full range of colors is possible, whilst if only two out of the three red, green and blue LEDs are provided, only a respective sub-range of colors can be obtained.

The output from the output device may be used to signal to the user various conditions or states within the e-cigarette, such as a low battery warning. Different output signals may be used for signaling different states or conditions. For example, if the output device 58 is an audio speaker, different states or conditions may be represented by tones or beeps of different pitch or duration, or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 38 is nearly depleted. It will be appreciated that a given e-cigarette may include output devices to support multiple different output modes (audio, visual) etc.

The input device(s) 59 may be provided in various forms. For example, an input device (or devices) may be implemented as buttons on the outside of the e-cigarette—e.g. as mechanical, electrical or capacitive (touch) sensors. Some devices may support blowing into the e-cigarette as an input mechanism (such blowing may be detected by pressure sensor 62, which would then be also acting as a form of input device 59), or connecting/disconnecting the cartomizer 30 and control unit 20 as another form of input mechanism. Again, it will be appreciated that a given e-cigarette may include input devices 59 to support multiple different input modes.

As noted above, the e-cigarette 10 provides an air path from the air inlet through the e-cigarette, past the pressure sensor 62 and the heater 310 in the cartomizer 30 to the mouthpiece 35. Thus when a user inhales on the mouthpiece of the e-cigarette, the processor 50 detects such inhalation based on information from the pressure sensor 62. In response to such a detection, the CPU supplies power from the battery 54 to the heater, which thereby heats and vaporizes the nicotine from the liquid reservoir 38 for inhalation by the user.

In the particular implementation shown in FIG. 2, a FET 210 is connected between the battery 54 and the connector 21A. This FET 210 acts as a switch. The processor 50 is connected to the gate of the FET to operate the switch, thereby allowing the processor to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET is on for all of each period (i.e. in effect, permanently on). It will be appreciated that these are only given as example settings for the duty cycle, and intermediate values can be used as appropriate.

The use of PWM provides an effective power to the heater which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to supply the heater 310 with the desired operating power As shown in FIG. 2, the processor 50 includes a communications interface 55 for wireless communications, in particular, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore may benefit from being more durable). The metal housing acts as a screen or barrier which can affect the operation of an antenna located within the control unit 20 itself. However, utilizing the heater 310 as the antenna for the wireless communications can help to avoid this metal screening because of the plastic housing of the cartomizer, but without adding additional components or complexity (or cost) to the cartomizer. Alternatively a separate antenna may be provided (not shown), or a portion of the metal housing may be used.

If the heater is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater is not powered for heating (as discussed in more detail below). It will be appreciated that capacitor 220 helps prevent the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching can help support proper transfer of signals between the communications interface 55 and the heater 310 acting as the antenna, rather than having such signals reflected back along the connection).

In some implementations, the processor 50 and communications interface are implemented using a Dialog DA14580 chip from Dialog Semiconductor PLC, based in Reading, United Kingdom. Further information (and a data sheet) for this chip is available at: http://www.dialog-semiconductor.com/products/bluetooth-smart/smartbond-da14580.

Figure 3:
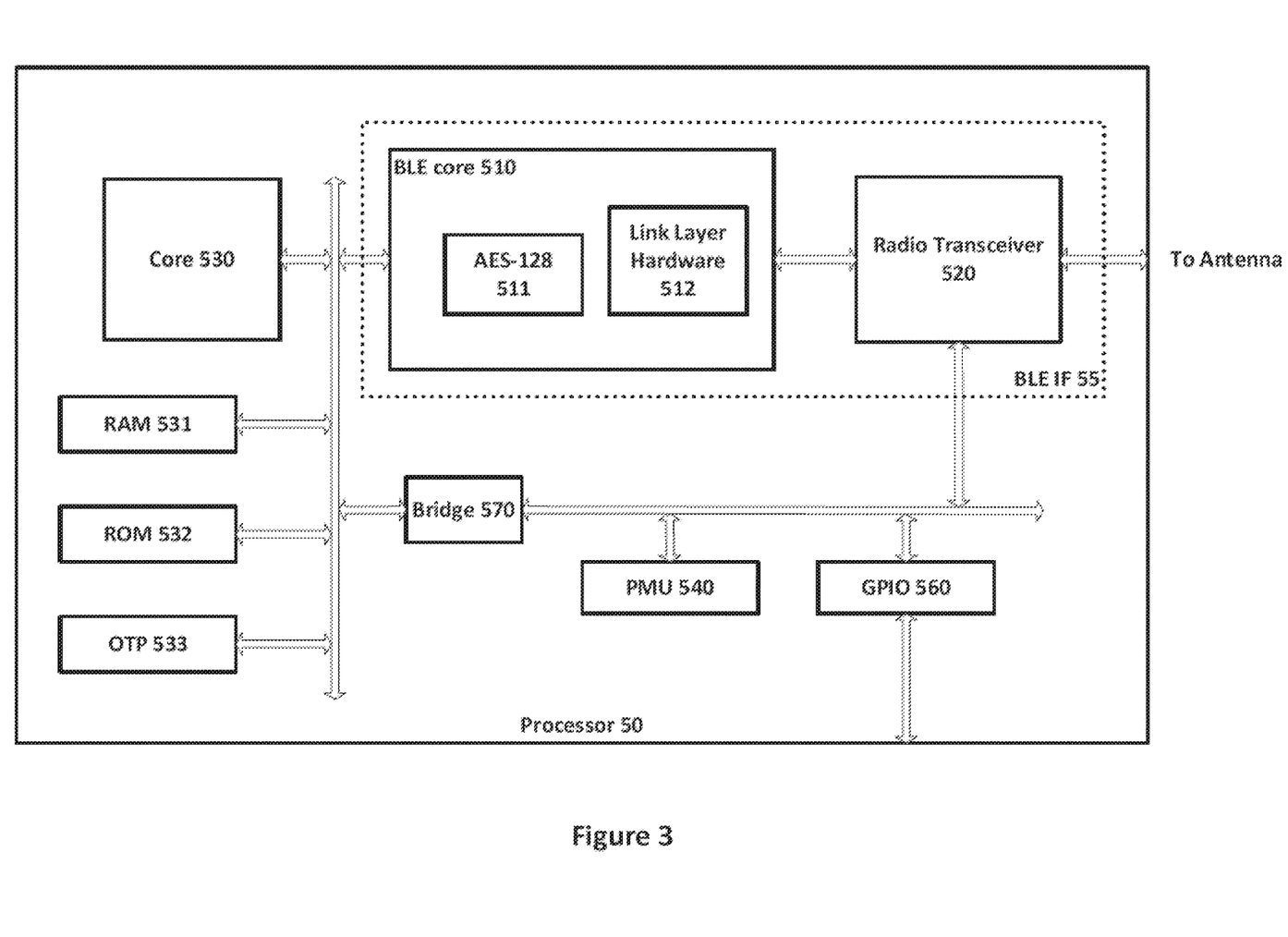
FIG. 3 is a schematic diagram of a processor of an e-cigarette in accordance with embodiments of the present invention.

FIG. 3 presents a high-level and simplified overview of this chip 50, including the communications interface 55 for supporting Bluetooth® Low Energy. This interface includes in particular a radio transceiver 520 for performing signal modulation and demodulation, etc, link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The remainder of processor 50 includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 or OTP unit 533 may be loaded into RAM 531 (or into memory provided as part of core 530) for execution by one or more processing units within core 530. These software instructions cause the processor 50 to implement various functionality described herein, such as interfacing with the sensor unit 61 and controlling the heater accordingly. Note that although the device shown in FIG. 3 acts as both a communications interface 55 and also as a general controller for the electronic vapor provision system 10, in other embodiments these two functions may be split between two or more different devices (chips)—e.g. one chip may serve as the communications interface 55, and another chip as the general controller for the electronic vapor provision system 10.

In some implementations, the processor 50 may be configured to prevent wireless communications when the heater is being used for vaporizing liquid from reservoir 38. For example, wireless communications may be suspended, terminated or prevented from starting when switch 210 is switched on. Conversely, if wireless communications are ongoing, then activation of the heater may be prevented— e.g. by disregarding a detection of airflow from the sensor unit 61, or by not operating switch 210 to turn on power to the heater 310 while the wireless communications are progressing.

One reason for preventing the simultaneous operation of heater 310 for both heating and wireless communications in some implementations is to help avoid potential interference from the PWM control of the heater. This PWM control has its own frequency (based on the repetition frequency of the pulses), albeit typically much lower than the frequency used for the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths or PWM frequency, the provision of suitable filtering, etc.

Figure 4:
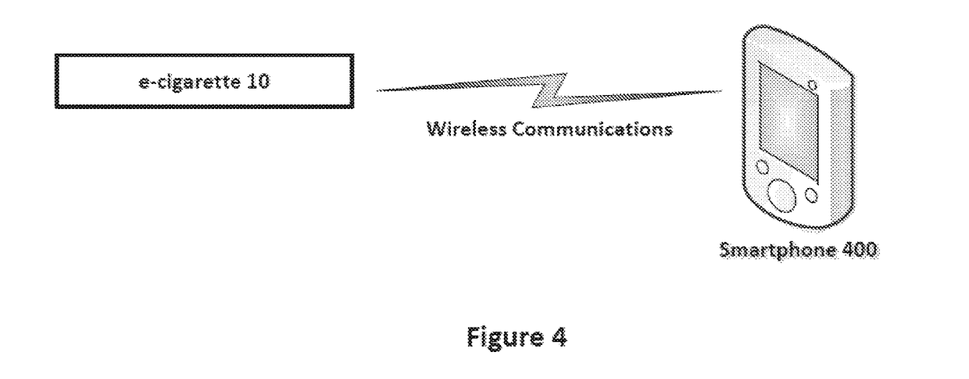
FIG. 4 is a schematic diagram of an e-cigarette in communication with a mobile terminal in accordance with embodiments of the present invention.

FIG. 4 is a schematic diagram showing Bluetooth® Low Energy communications between an e-cigarette 10 and an application (app) running on a smartphone 400 or other suitable mobile communication device (tablet, laptop, smartwatch, etc). Such communications can be used for a wide range of purposes, for example, to upgrade firmware on the e-cigarette 10, to retrieve usage or diagnostic data from the e-cigarette 10, to reset or unlock the e-cigarette 10, to control settings on the e-cigarette, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smartphone 400, then the smartphone 400 requests a connection to the e-cigarette 10. The e-cigarette may notify this request to a user via output device 58, and wait for the user to accept or reject the request via input device 59. Assuming the request is accepted, the e-cigarette 10 is able to communicate further with the smartphone 400. Note that the e-cigarette may remember the identity of smartphone 400 and be able to accept future connection requests automatically from that smartphone. Once the connection has been established, the smartphone 400 and the e-cigarette 10 operate in a client-server mode, with the smartphone operating as a client that initiates and sends requests to the e-cigarette which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth Low Energy link may extend up to some 50 m. However, for the situation shown in FIG. 4, the e-cigarette 10 and the smartphone 400 will typically belong to the same person, and will therefore be in much closer proximity to one another—e.g. 1 m. Further information about Bluetooth Low Energy can be found at: http://www.bluetooth.com/Pages/Bluetooth-Smart.aspx It will be appreciated that e-cigarette 10 may support other communications protocols for communication with smartphone 400 (or any other appropriate device). Such other communications protocols may be instead of, or in addition to, Bluetooth Low Energy. Examples of such other communications protocols include Bluetooth® (not the low energy variant), see for example, www.bluetooth.com, near field communications (NFC), as per ISO 13157, and WiFi®). NFC communications operate at much lower wavelengths than Bluetooth (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Figure 5:
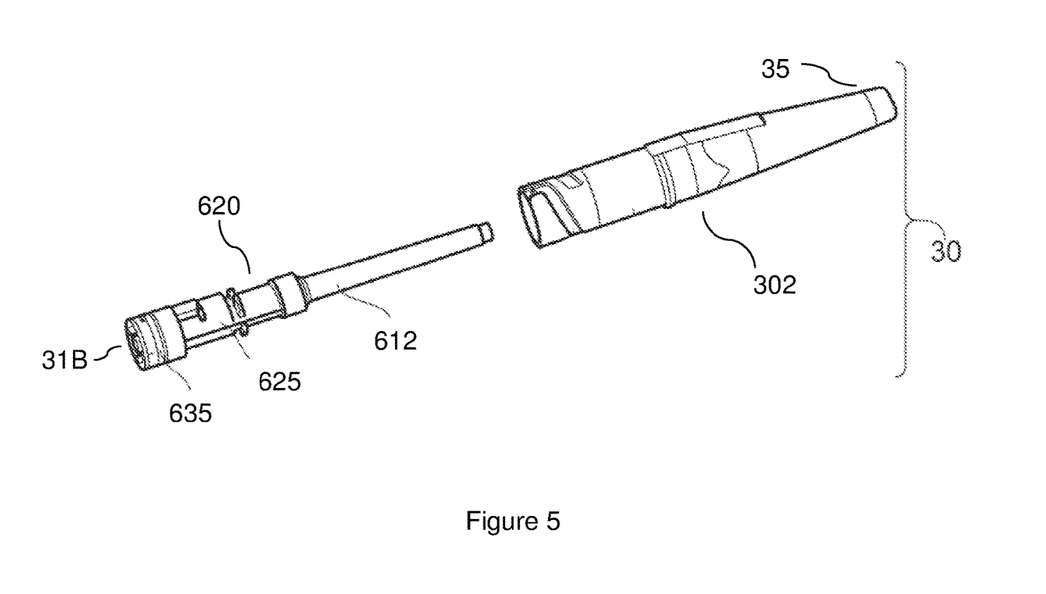
FIG. 5 is a schematic diagram of a cartomizer of an e-cigarette.

FIG. 5 is a schematic, exploded view of an example cartomizer 30 in accordance with some embodiments. The cartomizer has an outer plastic housing 302, a mouthpiece 35 (which may be formed as part of the housing), a vaporizer 620, a hollow inner tube 612, and a connector 31B for attaching to a control unit. An airflow path through the cartomizer 30 starts with an air inlet through connector 31B, then through the interior of vaporizer 625 and hollow tube 612, and finally out through the mouthpiece 35. The cartomizer 30 retains liquid in an annular region between (i) the plastic housing 302, and (ii) the vaporizer 620 and the inner tube 612. The connector 31B is provided with a seal 635 to help maintain liquid in this region and to prevent leakage.

Figure 6:
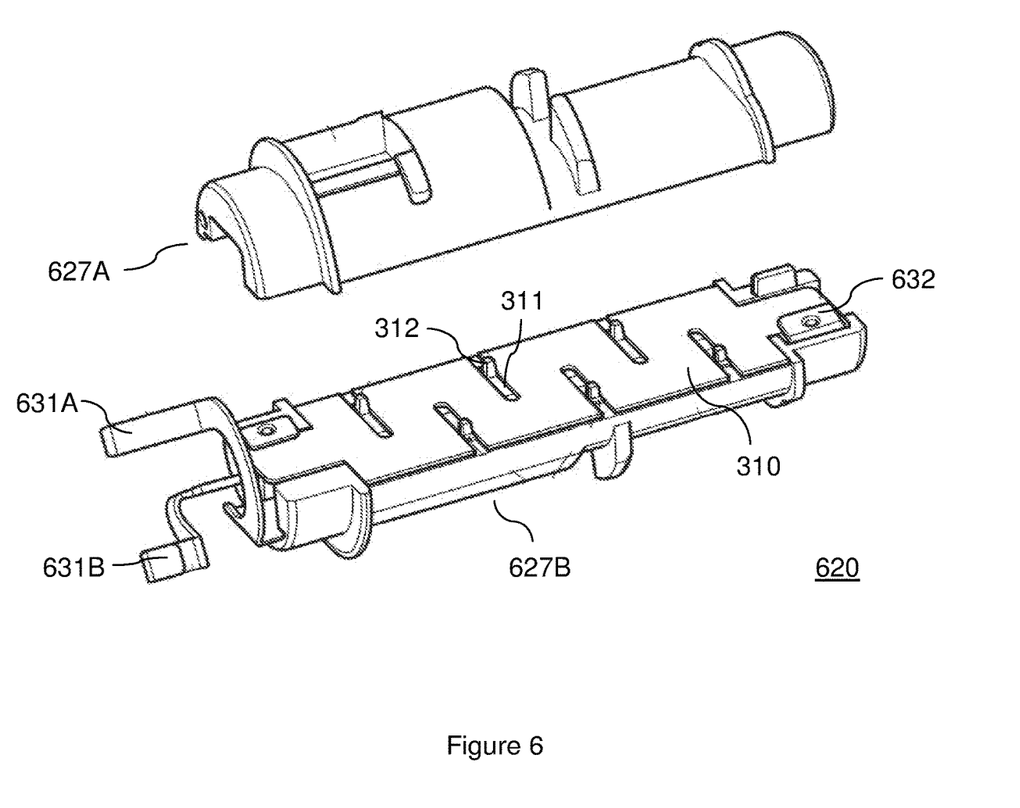
FIG. 6 is a schematic diagram of a vaporizer or heater of an e-cigarette.

FIG. 6 is a schematic, exploded view of the vaporizer 620 from the example cartomizer 30 shown in FIG. 5. The vaporizer 620 has a substantially cylindrical housing (cradle) formed from two components, 627A, 627B, each having a substantially semi-circular cross-section. When assembled, the edges of the components 627A, 627B do not completely abut one another (at least, not along their entire length), but rather a slight gap 625 remains (as indicated in FIG. 5). This gap allows liquid from the outer reservoir around the vaporizer and tube 612 to enter into the interior of the vaporizer 620.

One of the components 627B of the vaporizer is shown in FIG. 6 supporting a heater 310. There are two connectors 631A, 631B shown for supplying power (and a wireless communication signal) to the heater 310. More particular, these connectors 631A, 631B link the heater to connector 31B, and from there to the control unit 20. (Note that connector 631A is joined to pad 632A at the far end of vaporizer 620 from connector 31B by an electrical connection that passes under the heater 310 and which is not visible in FIG. 6).

The heater 310 comprises a heating element formed from a sintered metal fiber material and is generally in the form of a sheet or porous, conducting material (such as steel). However, it will be appreciated that other porous conducting materials may be used. The overall resistance of the heating element in the example of FIG. 6 is around 1 ohm. However, it will be appreciated that other resistances may be selected, for example having regard to the available battery voltage and the desired temperature/power dissipation characteristics of the heating element. In this regard, the relevant characteristics may be selected in accordance with the desired aerosol (vapor) generation properties for the device depending on the source liquid of interest.

The main portion of the heating element is generally rectangular with a length (i.e. in a direction running between the connector 31B and the contact 632A) of around 20 mm and a width of around 8 mm. The thickness of the sheet comprising the heating element in this example is around 0.15 mm.

As can be seen in FIG. 6, the generally-rectangular main portion of the heating element has slots 311 extending inwardly from each of the longer sides. These slots 311 engage pegs 312 provided by vaporizer housing component 627B, thereby helping to maintain the position of the heating element in relation to the housing components 627A, 627B.

The slots extend inwardly by around 4.8 mm and have a width of around 0.6 mm. The slots 311 extending inwardly are separated from one another by around 5.4 mm on each side of the heating element, with the slots extending inwardly from the opposing sides being offset from one another by around half this spacing. A consequence of this arrangement of slots is that current flow along the heating element is in effect forced to follow a meandering path, which results in a concentration of current and electrical power around the ends of the slots. The different current/power densities at different locations on the heating element mean there are areas of relatively high current density that become hotter than areas of relatively low current density. This in effect provides the heating element with a range of different temperatures and temperature gradients, which can be desirable in the context of aerosol provision systems. This is because different components of a source liquid may aerosolize/vaporize at different temperatures, and so providing a heating element with a range of temperatures can help simultaneously aerosolize a range of different components in the source liquid.

The heater 310 shown in FIG. 6, having a substantially planar shape which is elongated in one direction, is well-suited to act as an antenna. In conjunction with the metal housing 202 of the control unit, the heater 310 forms an approximate dipole configuration, which typically has a physical size of the same order of magnitude as the wavelength of Bluetooth Low Energy communications—i.e. a size of several centimetres (allowing for both the heater 310 and the metal housing 202) against a wavelength of around 12 cm.

Although FIG. 6 illustrates one shape and configuration of the heater 310 (heating element), the skilled person will be aware of various other possibilities. For example, the heater may be provided as a coil or some other configuration of resistive wire. Another possibility is that the heater is configured as a pipe containing liquid to be vaporized (such as some form of tobacco product). In this case, the pipe may be used primarily to transport heat from a place of generation (e.g. by a coil or other heating element) to the liquid to be vaporized. In such a case, the pipe still acts as a heater in respect of the liquid to be heated. Such configurations can again optionally be used as an antenna to support wireless configurations.

As was noted previously herein, a suitable e-cigarette 10 can communicate with a mobile communication device 400, for example by paring the devices using the Bluetooth® low energy protocol.

Consequently, it is possible to provide additional functionality to the e-cigarette or to a system comprising the e-cigarette and the smart phone, by providing suitable software instructions (for example in the form of an app) to run on the smart phone.

Figure 7:
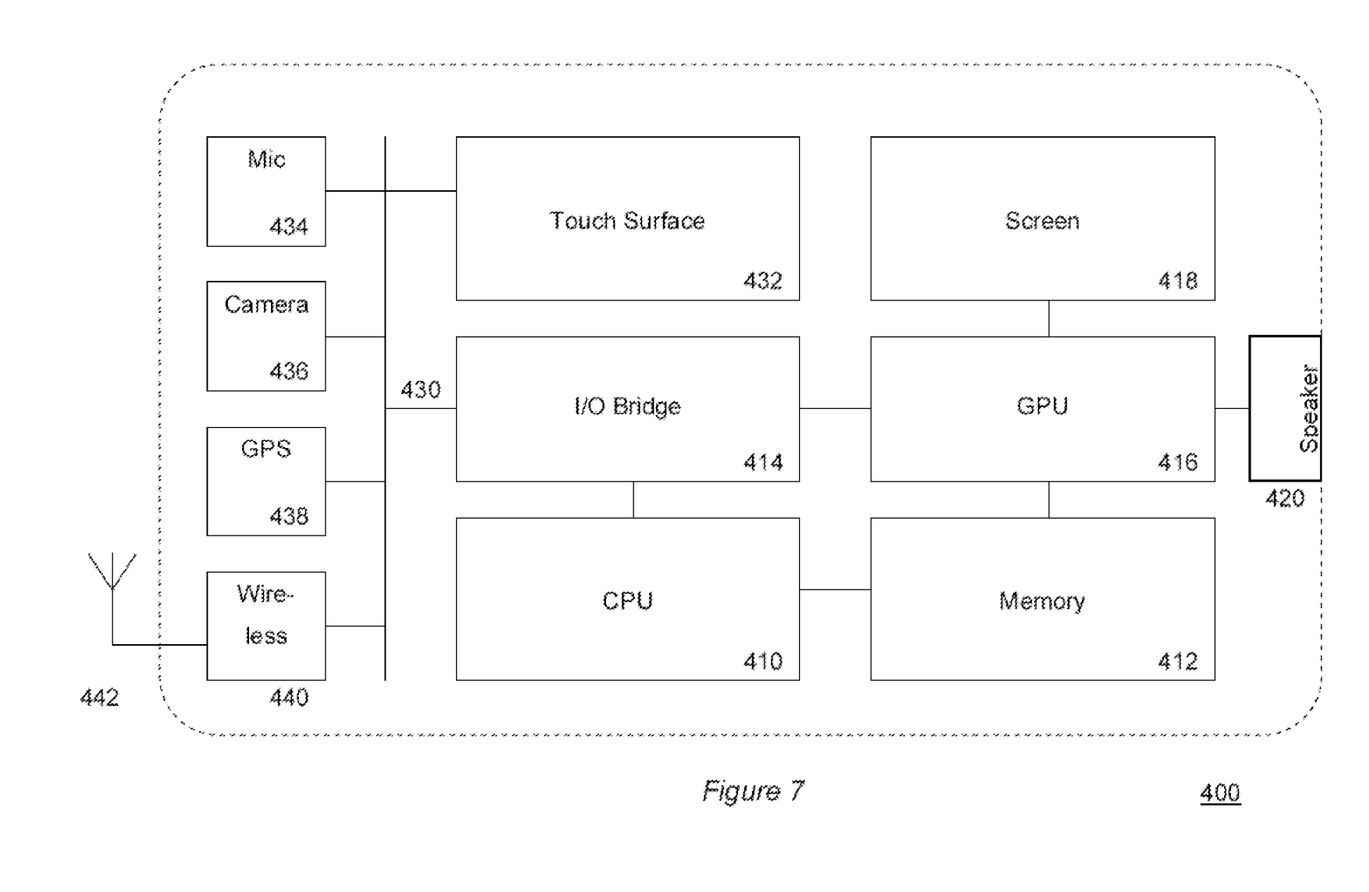
FIG. 7 is a schematic diagram of a mobile terminal in accordance with embodiments of the present invention.

Turning now to FIG. 7, a typical smartphone 400 comprises a central processing unit (CPU) (410). The CPU may communicate with components of the smart phone either through direct connections or via an I/O bridge 414 or a bus 430 as applicable.

In the example shown in FIG. 7, the CPU communicates directly with a memory 412, which may comprise a persistent memory such as for example Flash® memory for storing an operating system and applications (apps), and volatile memory such as RAM for holding data currently in use by the CPU. Typically persistent and volatile memories are formed by physically distinct units (not shown). In addition, the memory may separately comprise plug-in memory such as a microSD card, and also subscriber information data on a subscriber information module (SIM) (not shown).

The smart phone may also comprise a graphics processing unit (GPU) 416. The GPU may communicate directly with the CPU or via the I/O bridge, or may be part of the CPU. The GPU may share RAM with the CPU or may have its own dedicated RAM (not shown) and is connected to the display 418 of the mobile phone. The display is typically a liquid crystal (LCD) or organic light-emitting diode (OLED) display, but may be any suitable display technology, such as e-ink. Optionally the GPU may also be used to drive one or more loudspeakers 420 of the smart phone.

Alternatively, the speaker may be connected to the CPU via the I/O bridge and the bus. Other components of the smart phone may be similarly connected via the bus, including a touch surface 432 such as a capacitive touch surface overlaid on the screen for the purposes of providing a touch input to the device, a microphone 434 for receiving speech from the user, one or more cameras 436 for capturing images, a global positioning system (GPS) unit 438 for obtaining an estimate of the smart phones geographical position, and wireless communication means 440.

The wireless communication means 440 may in turn comprise several separate wireless communication systems adhering to different standards or protocols, such as Bluetooth® (standard or low-energy variants), near field communication and Wi-Fi® as described previously, and also phone based communication such as 2G, 3G or 4G.

The systems are typically powered by a battery (not shown) that may be chargeable via a power input (not shown) that in turn may be part of a data link such as USB (not shown). It will be appreciated that different smartphones may include different features (for example a compass or a buzzer) and may omit some of those listed above (for example a touch surface). Thus more generally, in an embodiment of the present disclosure a suitable remote device such as smart phone 400 will comprise a CPU and a memory for storing and running an app, and wireless communication means operable to instigate and maintain wireless communication with the e-cigarette 10. It will be appreciated however that the remote device may be a device that has these capabilities, such as a tablet, laptop, smart TV or the like.

In an embodiment of the present invention, an active ingredient adjustment system for an electronic vapor provision system (EVPS) such as e-cigarette 10, comprises a memory adapted to store data indicating a target amount of active ingredient to be delivered by the EVPS within a predetermined period having a predetermined start point. The memory may be RAM within or associated with a processor 50 of the EVPS. Alternatively or in addition, the memory may be part of a remote device such as a mobile phone that in wireless communication with the EVPS, typically periodically as in the case of a Bluetooth® Low Energy (BLE) connection.

The data can take the form of one or more target amounts of active ingredient, or proxies for that target amount, such as a target amount of payload where the concentration of active ingredient within the payload is known, assumed or detected, as discussed later herein.

The active ingredient adjustment system also comprises a payload usage sensor operable to detect the amount of payload being used. Any suitable sensor may be considered, such as a sensor measuring electrical properties of a payload reservoir that vary according to the amount of payload inside (for example changes in capacitance or resistance as a function of the amount of payload), or an optical sensor operable to measure the amount of liquid according to the amount of light transmitted or absorbed through the reservoir, or any other suitable measurement technique (for example through ultrasound propagation/reflection within the payload). Alternatively the amount of payload being used may be calculated for example based upon inhalation time and measured airflow, which together may be used to determine the volume of vaporized payload drawn out of the EVPS by the user. Hence for example sensor unit 61, comprising pressure sensor 62, may act as a payload usage sensor in combination with a calculation relating pressure drop to airflow speed which with the cross-section area of the channel comprising the pressure sensor enables a calculation of flow volume. The amount of vaporized payload in a unit volume of air may then be determined empirically, optionally for different pressures/airflow speeds where this affects the amount.

The active ingredient adjustment system also comprises a usage timing processor operable to calculate the rate of active ingredient being delivered to the user based upon the amount of payload being used. Again this usage timing processor may be the built-in processor 50 of the EVPS operating under suitable software instruction, or may be a processor of a remote device such as a phone that is in wireless communication with the EVPS.

Notably the rate of active ingredient being delivered to the user is calculated, thereby estimating the amount of active ingredient being delivered to the user over a unit period of time. As such it is not merely a count of the number of puffs performed by the user, either counting up or counting down to a preset limit.

The active ingredient adjustment system then also comprises an adjustment processor adapted to alter the operation of the EVPS, if the usage timing processor calculates a rate of active ingredient being delivered that will result in exceeding the target within the predetermined period, to reduce the rate of active ingredient being delivered to the user.

Again this adjustment processor may be the built-in processor 50 of the EVPS operating under suitable software instruction, or may be a processor of a remote device such as a phone that is in wireless communication with the EVPS.

It will be appreciated that the active ingredient adjustment system therefore sets a target amount of active ingredient to be consumed within a predetermined period of time, and then calculates whether the user's rate of consumption will result in missing the target amount at a predetermined time in the future, and adapting the operation of the EVPS now to prevent that from occurring.

Optionally, the operation of the EVPS is only adapted if it is calculated that the user's rate of consumption will result in exceeding the target amount at the predetermined time in the future.

To give a specific but non-limiting example, a user may wish to imbibe 24 mg of nicotine per day. The predetermined period is therefore one day, having a predetermined start point that may correspond with midnight (i.e. one calendar day) or may correspond with another time, such as 4 AM, to accommodate the possibility that the user may stay out late into the evening and therefore their cycle of usage resets in the early hours of the morning rather than midnight. It will also be appreciated that 'one day' may be defined to correspond to the user's normal waking period, for example between 7 AM and 11 PM. Hence for example a user may specify the effective period for one day, for example via a UI on a mobile phone.

During use of the EVPS over the course of the day, the payload usage sensor detects amount of payload being used, and the usage timing processor calculates the equivalent amount of active ingredient being used during a unit period of time, such as one hour. From this, the usage timing processor can calculate a delivery rate of mg/hr of nicotine, in this example.

The adjustment processor keeps a record of the amount of active ingredient consumed so far within the predetermined period, and hence how much active ingredient may still be consumed during the remainder of the predetermined period before reaching the target amount.

If the current rate of consumption, multiplied by the time remaining in the predetermined period, exceeds the amount of active ingredient that may still be consumed, then the adjustment processor can predict that the user will exceed the target amount within the predetermined period.

In this case, the just processor can alter the operation of the EVPS to reduce the rate of active ingredient being delivered to the user.

This can be done in one or more ways.

In a first instance, heating of the payload to form a vapor is time-limited during each puff action by the user. For example, if the typical inhalation period by a user is 0.75 seconds, then limiting the heating period to 0.5 seconds reduces the amount of payload being consumed by approximately one third.

In another instance, heating of the payload to form a vapor is performed according to a duty cycle, such as 0.1 seconds on, 0.05 seconds off. In this way, one third less vapor is generated for the duration of the user's inhalation.

It will be appreciated that any suitable timing or duty cycle may be chosen in order to adjust the amount of vapor being delivered, responsive to the extent to which the current rate of consumption is likely to cause the user to exceed the target amount by the end of the predetermined period.

Other techniques may similarly be used, such as reducing the heating temperature, and reducing the airflow within the EVPS.

It will be appreciated that any suitable combination of these techniques, or any other technique that serves to reduce the amount of vapor generated during a user's puff, may be employed.

The active ingredient adjustment system may also comprise a clock. Again the clock may be part of the EVPS system or part of a remote device such as a phone in wireless communication with the EVPS.

The adjustment processor may then be adapted to set the predetermined start point when the clock equals a predetermined time (for example midnight or 4 AM, as discussed previously herein, or any chosen time).

Alternatively or in addition, the active ingredient adjustment system may receive a 'start' signal from a separate device, or by user activation (for example by pressing a button before a first puff of the day), denoting the predetermined start point.

In an embodiment of the present invention, the adjustment processor is adapted to calculate the amount of active ingredient remaining in the EVPS, and the adjustment processor is adapted to set the predetermined start point when the calculated amount equals the target amount.

In this case, the adjustment processor may maintain a measure of the amount of payload consumed since the current payload was mounted within the EVPS (for example when a new e-liquid reservoir or payload cartridge was inserted into the EVPS). When the original amount of payload minus the cumulative amount of payload consumed equals a target amount, then a predetermined period is started.

This predetermined period may provide the user with sufficient time to purchase or otherwise obtain a replacement payload for the EVPS, such as for example one full day of 24 hours, or until a predetermined time of day, such as before 10 PM on the current day.

The adjustment processor can then monitor the rate of consumption of the user and predict whether the user will run out of payload before the end of the predetermined period, and if so then adjust the rate of active ingredient being delivered to the user so that the remaining payload lasts until the end of the predetermined period, thereby giving the user sufficient time to obtain a replacement before completely running out of payload.

In this way, an EVPS can enact a payload saving mode in which the consumption of payload is adjusted if the rate of consumption by the user means they are likely to run out of payload before a predetermined period has elapsed.

It will be appreciated that the target amount for a payload saving mode may be different to a user-set target amount. Hence for example a user may set a target amount of 24 mg nicotine per day as a self-imposed limit. However the target amount for a payload saving mode may be 10 mg nicotine. Meanwhile the predetermined period over which the payload is conserved may be one day, 10 hours, one hour or any suitable period within which it is reasonable to assume the user can obtain a replacement payload for the EVPS.

Hence will be appreciated that a different predetermined period may be selected according to the respective criterion upon which the predetermined start point are selected, with a period for a user set target amount potentially being different to the period for a payload saving mode target amount.

In an embodiment of the present invention, a payload concentration sensors operable to detect the concentration of active ingredient within the payload. Typically this detection will be by detection of an indicator of concentration rather than by direct measurement of payload, although such direct measurement may optionally be implemented where practical.

By default, the concentration of active ingredient within the payload may be assumed to be a preset level, for example a level used by the manufacturer of the particular EVPS. However, optionally this may be supplanted by a detected concentration level, for example signified by the presence or absence of electrical contacts on the payload container, defining a binary pattern corresponding to a concentration of active ingredient, or a shape of a portion of a payload container that interact with sensors e.g. switches within the EVPS, again defining a binary pattern corresponding to a concentration of active ingredient. Alternatively or in addition, the concentration of may be detected by reference to information on payload container packaging, such as a barcode or QR code scanned by an application on a mobile device operable to read active ingredient concentration information from the scanned code or from a data source indicated by the scanned code, and then use this information itself in the case that it also acts as the usage timing processor or adjustment processor, or convey this information to the EVPS in the case that the EVPS processor acts as the usage timing processor or adjustment processor.

As noted previously herein, the user may set a target amount, and optionally also a predetermined period. Accordingly, the active ingredient adjustment system may comprise an input adapted to receive an indication from a user of the target amount. This input may be provided on the EVPS; for example, pressing a button may cycle through a set of predefined target values such as 10, 15, 20, and 30 mg, with a light or beep be activated when the cycle resets. The user can then set the target value with a minimal user interface. Alternatively or in addition, an app on a mobile device may provide a richer user interface through which a user can specify a preferred target value, and optionally a preferred predetermined time, for example specifying a start time and end time for an effective day.

In an embodiment of the present invention, the active ingredient adjustment system comprises a geographical position detector operable to detect a geographical location of the EVPS. Typically this will be a GPS receiver. The GPS receiver may be part of the EVPS, or may be part of a remote device operable to wirelessly communicate with the EVPS such as a mobile phone. In this latter case it can be assumed that when the remote device is in communication with the EVPS, they are sufficiently closely co-located that the position of the remote device is a sufficiently accurate proxy for the location of the EVPS. Alternative means of detecting geographical position may be a country code within a mobile network signal, for example.

The active ingredient adjustment system can set a target amount in response to the detected geographical location of the EVPS. In this way, the active ingredient adjustment system can for example set a maximum amount of active ingredient to be consumed per day, or per hour, etc., where that maximum amount is no more than the legal maximum imposed by the country, state or other legislative entity corresponding to the detected geographical location. In this way, in principle a user can inhale on their EVPS as often as they wish, safe in the knowledge that they are not breaking the law. This may be of particular use in countries or states where psychoactive drugs such as marijuana are legalized, but where there are penalties for driving or other activities after consuming more than a certain amount of the drug, or having more than a certain concentration of the drug in the bloodstream.

It will also be appreciated that by calculating and monitoring the rate of consumption, the active ingredient adjustment system can detect if an effective bolus of drug is in the process of being consumed over a relatively short term period, which may temporarily take the user above a legal limit (for example, if the user attempts to inhale a day's worth of active ingredient within two hours), and act to reduce the amount of active ingredient being supplied if the current rate of consumption indicates that a bolus may occur.

Hence more generally, in addition to adjusting operation of an EVPS to reduce a rate of active ingredient being delivered to a user so that they reach (or do not exceed) a target by a future time, the adjustment processor is optionally operable to adjusting operation of an EVPS to reduce a rate of active ingredient being delivered to a user when this exceed a threshold rate of consumption. This threshold rate may be set by the user, or may be imposed based on pre-set legal requirements associated with the location of the EVPS (optionally either the location as sold, or as detected by the active ingredient adjustment system).

As noted elsewhere herein, it will be appreciated that at least one of the usage timing processor, the adjustment processor and the memory may be located on a device remote to the EVPS, such as a mobile phone, which is in wireless communication with it, typically on at a periodic basis.

Hence more generally in an embodiment of the present invention an EVPS 10 may comprise an active ingredient adjustment system that in turn comprises a payload usage sensor 61 operable to detect the amount of payload being used, the active ingredient adjustment system being adapted to alter operation of the EVPS in response to control signals from an adjustment processor adapted to alter the operation of the EVPS to reduce the rate of active ingredient being delivered to a user of the EVPS, if a usage timing processor calculates a rate of active ingredient being delivered that will result in exceeding a target amount of active ingredient to be delivered by the VPS within a predetermined period having a predetermined start point.

The EVPS itself may then comprise at least one of the adjustment processor and the usage timing processor, for example in the form of processor EVPS 50 operating under suitable software instruction. Any components not included in the EVPS may then be provided via a remote device in wireless communication with the EVPS, as described herein. The active ingredient adjustment system or the EVPS may also comprise the memory adapted to store data indicating a target amount of active ingredient to be delivered by the EVPS within a predetermined period having a predetermined start point.

Similarly, more generally in an embodiment of the present invention a mobile communication device 400 may comprise a wireless receiver 440 (e.g. Bluetooth WiFi® etc) adapted to receive data from an electronic vapor provision system (EVPS) indicative of an amount of payload being used by a user; and a wireless transmitter 440 (e.g. Bluetooth WiFi® etc) adapted to transmit control data to the EVPS, and an active ingredient adjustment system (for example, CPU 410 operating under suitable software instruction) in turn comprising a usage timing processor (for example, CPU 410 operating under suitable software instruction) operable to calculate the rate of active ingredient being delivered to the user based upon the amount of payload being used; and an adjustment processor (for example, CPU 410 operating under suitable software instruction) adapted to generate control data for altering the operation of the EVPS to reduce the rate of active ingredient being delivered to the user, if the usage timing processor calculates a rate of active ingredient being delivered that will result in exceeding a target within a predetermined period having a predetermined start point.

Figure 8:
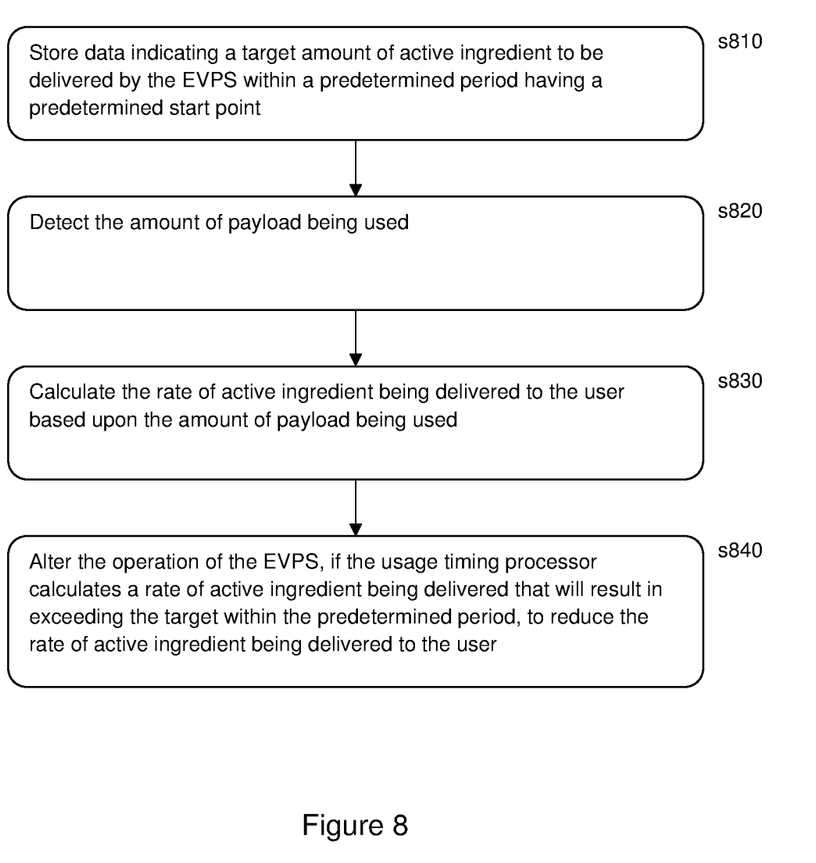
FIG. 8 is a flow diagram of a method of active ingredient adjustment in accordance with embodiments of the present invention.

Turning now to FIG. 8, a method of active ingredient adjustment for an electronic vapor provision system (EVPS) comprises:

in a first step s810, storing data indicating a target amount of active ingredient to be delivered by the EVPS within a predetermined period having a predetermined start point;

in a second step s820, detecting the amount of payload being used;

in a third step s830, calculating the rate of active ingredient being delivered to the user based upon the amount of payload being used; and in a fourth step s840, altering the operation of the EVPS, if the usage timing processor calculates a rate of active ingredient being delivered that will result in exceeding the target within the predetermined period, to reduce the rate of active ingredient being delivered to the user.

It will be apparent to a person skilled in the art that variations in the above method corresponding to operation of the various embodiments of the apparatus as described and claimed herein are considered within the scope of the present invention, including but not limited to:

the predetermined start point being a predetermined time of day;

the method comprising the steps of calculating the amount of active ingredient remaining in the EVPS, and setting the predetermined start point when the calculated amount equals the target amount;

the method comprising the steps of detecting the concentration of active ingredient within the payload, and calculating the rate of active ingredient being delivered to the user based upon the amount of payload being used and the detected concentration of active ingredient within the payload;

the method comprising the steps of detecting a geographical location of the EVPS, and setting the target amount responsive to the detected geographical location of the EVPS; and at least one of the steps of calculating the rate of active ingredient being delivered to the user, and altering the operation of the e-cigarette, is performed by a device remote to the e-cigarette and in wireless communication with it.

It will be appreciated that the above methods may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

The invention claimed is:

1. An active ingredient adjustment system for an electronic vapor provision system (EVPS), comprising:
    a memory adapted to store data indicating a target amount of active ingredient to be delivered by the EVPS within a predetermined period having a predetermined start point and a predetermined end point;
    a payload usage sensor configured to detect the amount of payload being used;
    a usage timing processor configured to calculate the rate of active ingredient being delivered to the user based upon the amount of payload being used; and
    an adjustment processor configured to alter the operation of the EVPS to reduce the rate of active ingredient being delivered to the user in response to the usage timing processor calculating a rate of active ingredient being delivered that will result in exceeding the target within the predetermined period,
    wherein at the predetermined end point the payload of the EVPS is depleted, and
    wherein the adjustment processor is adapted to calculate the amount of active ingredient remaining in the EVPS, and the adjustment processor is adapted to set the predetermined start point when the calculated amount of active ingredient remaining in the EVPS equals the target amount.

2. A system according to claim 1, comprising:
    a clock;
    wherein the adjustment processor is configured to set the predetermined start point when the clock equals a predetermined time.

3. A system according to claim 1, wherein a different predetermined period is selected according to a respective criterion upon which the predetermined start point is selected.

4. A system according to claim 1, further comprising:
a payload concentration sensor configured to detect the concentration of active ingredient within the payload; and in which
the usage timing processor is configured to calculate the rate of active ingredient being delivered to the user based upon the amount of payload being used and the detected concentration of active ingredient within the payload.

5. A system according to claim 1, further comprising:
an input adapted to receive an indication from a user of the target amount.

6. A system according to claim 1, further comprising:
a geographical position detector configured to detect a geographical location of the EVPS;
wherein the target amount is set responsive to the detected geographical location of the EVPS.

7. A system according to claim 1, wherein at least one of the usage timing processor and the adjustment processor is located on a device remote to the EVPS and in wireless communication with it.

8. A system according to claim 7, wherein the memory is located on the remote device.

9. An electronic vapor provision system (EVPS), comprising
an active ingredient adjustment system comprising:
a payload usage sensor operable to detect the amount of payload being used; and
the active ingredient adjustment system being configured to alter operation of the EVPS in response to control signals from an adjustment processor configured to alter the operation of the EVPS to reduce the rate of active ingredient being delivered to a user of the EVPS in response to a usage timing processor calculating a rate of active ingredient being delivered that will result in exceeding a target amount of active ingredient to be delivered by the VPS within a predetermined period having a predetermined start point and a predetermined end point,
wherein at the predetermined end point the payload of the EVPS is depleted,
wherein the adjustment processor is adapted to calculate the amount of active ingredient remaining in the EVPS, and the adjustment processor is adapted to set the predetermined start point when the calculated amount of active ingredient remaining in the EVPS equals the target amount.

10. An electronic vapor provision system according to claim 9, in which the EVPS comprises at least one of the adjustment processor and the usage timing processor.

* * * * *